United States Patent
Govari

(10) Patent No.: US 10,492,704 B2
(45) Date of Patent: Dec. 3, 2019

(54) MEDICAL PATCH FOR SIMULTANEOUSLY SENSING ECG SIGNALS AND IMPEDANCE-INDICATIVE ELECTRICAL SIGNALS

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 137 days.

(21) Appl. No.: 15/689,177

(22) Filed: Aug. 29, 2017

(65) Prior Publication Data

US 2019/0059759 A1 Feb. 28, 2019

(51) Int. Cl.

| A61B 5/04 | (2006.01) |
|---|---|
| A61B 5/0408 | (2006.01) |
| A61B 5/00 | (2006.01) |
| A61B 5/053 | (2006.01) |
| A61B 5/0428 | (2006.01) |

(52) U.S. Cl.
CPC ........ *A61B 5/0408* (2013.01); *A61B 5/04017* (2013.01); *A61B 5/0428* (2013.01); *A61B 5/053* (2013.01); *A61B 5/6833* (2013.01); *A61B 2560/0412* (2013.01)

(58) Field of Classification Search
CPC . A61B 5/0408; A61B 5/04017; A61B 5/6833; A61B 5/053; A61B 5/0428; A61B 2560/0412
See application file for complete search history.

(56) References Cited

U.S. PATENT DOCUMENTS

| 2003/0078510 A1 | 4/2003 | Olson et al. |
|---|---|---|
| 2006/0020218 A1 | 1/2006 | Freeman et al. |
| 2006/0030781 A1 | 2/2006 | Shennib |
| 2009/0318793 A1 | 12/2009 | Keshava et al. |
| 2010/0286607 A1 | 11/2010 | Saltzstein |
| 2012/0165644 A1 | 6/2012 | Schultz et al. |
| 2014/0094707 A1 | 4/2014 | Farringdon et al. |
| 2015/0141798 A1 | 5/2015 | Bar-Tal |
| 2016/0183876 A1 | 6/2016 | Shah et al. |

FOREIGN PATENT DOCUMENTS

EP 3181046 A1 6/2017

OTHER PUBLICATIONS

Extended European search report for corresponding European patent application No. 18191160.3, dated Jan. 23, 2019.

*Primary Examiner* — Mallika D Fairchild
(74) *Attorney, Agent, or Firm* — Notaro, Michalos & Zaccaria P.C.

(57) ABSTRACT

A medical patch includes a substrate, an electrode, and circuitry. The substrate is configured to attach externally to a patient. The electrode is coupled to the substrate and is configured to sense electrocardiogram (ECG) signals from a heart of the patient, and to further sense electrical signals indicative of an impedance between the electrode and a probe in the heart. The circuitry is coupled to the substrate and includes a shared amplifier that is configured to simultaneously amplify the ECG signals and the electrical signals sensed by the electrode.

8 Claims, 2 Drawing Sheets

MEDICAL PATCH FOR SIMULTANEOUSLY SENSING ECG SIGNALS AND IMPEDANCE-INDICATIVE ELECTRICAL SIGNALS

FIELD OF THE INVENTION

The present invention relates generally to sensing signals in patient organs, and particularly to methods and systems for sensing electrocardiogram (ECG) signals and impedance-indicative electrical signals.

BACKGROUND OF THE INVENTION

Multifunctional reference patches are used in various medical applications.

For example, U.S. Patent Application Publication 2012/0165644 describes a patch and sensor assembly that has a magnetic-based biosensor. The assembly is housed in a reusable portion that connects to the mapping and localization system via biosensor wires, and a disposable portion provides an electrode layer through which impedance-based signals are transmitted to the mapping and localization system via ACL wires.

U.S. Patent Application Publication 2009/0318793 describes a patch and sensor assembly for use in an electrophysiological (EP) mapping system. The assembly has two portions: a reusable portion and a disposable portion. The reusable portion houses the biosensors used in magnetic based location and mapping systems and the electrical lead necessary to communicate between the biosensor and the mapping system. The disposable portion of the patch and sensor assembly contains an adhesive covered flexible patch having at least a portion of the electrode used to receive electrical signals form the body of the patient and may contain the electrical lead necessary to communicate such an electrical signal to the mapping system.

U.S. Patent Application Publication 2014/0094707 describes a catheterization system that includes a monitor device and associated methodology which provide a self-contained, relatively small and continuously wearable package for the monitoring of heart related parameters, including ECG.

SUMMARY OF THE INVENTION

An embodiment of the present invention that is described herein provides a medical patch including a substrate, an electrode, and circuitry. The substrate is configured to attach externally to a patient. The electrode is coupled to the substrate and is configured to sense electrocardiogram (ECG) signals from a heart of the patient, and to further sense electrical signals indicative of an impedance between the electrode and a probe in the heart. The circuitry is coupled to the substrate and includes a shared amplifier that is configured to simultaneously amplify the ECG signals and the electrical signals sensed by the electrode.

In some embodiments, the circuitry includes first and second filters, which are configured to filter amplified ECG signals and amplified electrical signals, respectively, from an output of the amplifier. In other embodiments, the first and second filters cover respective first and second frequency ranges that differ from one another.

In an embodiment, the first and second frequency ranges are non-overlapping. In another embodiment, the amplifier has a dynamic range that covers both amplitudes of the received ECG signals and of the received electrical signals.

There is additionally provided, in accordance with an embodiment of the present invention, a method for producing a medical patch, the method that includes coupling, to a substrate configured to attach externally to a patient, an electrode for sensing electrocardiogram (ECG) signals from a heart of the patient, and for further sensing electrical signals indicative of an impedance between the electrode and a probe in the heart. Circuitry that includes a shared amplifier for simultaneously amplifying the ECG signals and the electrical signals sensed by the electrode, is coupled to the substrate.

There is further provided, in accordance with an embodiment of the present invention, a method that includes sensing, by an electrode coupled to a substrate attached externally to a patient, electrocardiogram (ECG) signals from a heart of the patient, and electrical signals indicative of an impedance between the electrode and a probe in the heart. The ECG signals and the electrical signals sensed by the electrode are amplified simultaneously, using circuitry that includes a shared amplifier coupled to the substrate. A medical procedure is performed, using amplified ECG signals and amplified electrical signals from an output of the amplifier.

In some embodiments, performing the medical procedure includes monitoring the heart based on the amplified ECG signals, and tracking a position of the probe in the heart based on the amplified electrical signals.

The present invention will be more fully understood from the following detailed description of the embodiments thereof, taken together with the drawings in which:

DETAILED DESCRIPTION OF EMBODIMENTS

Overview

Figure 1:
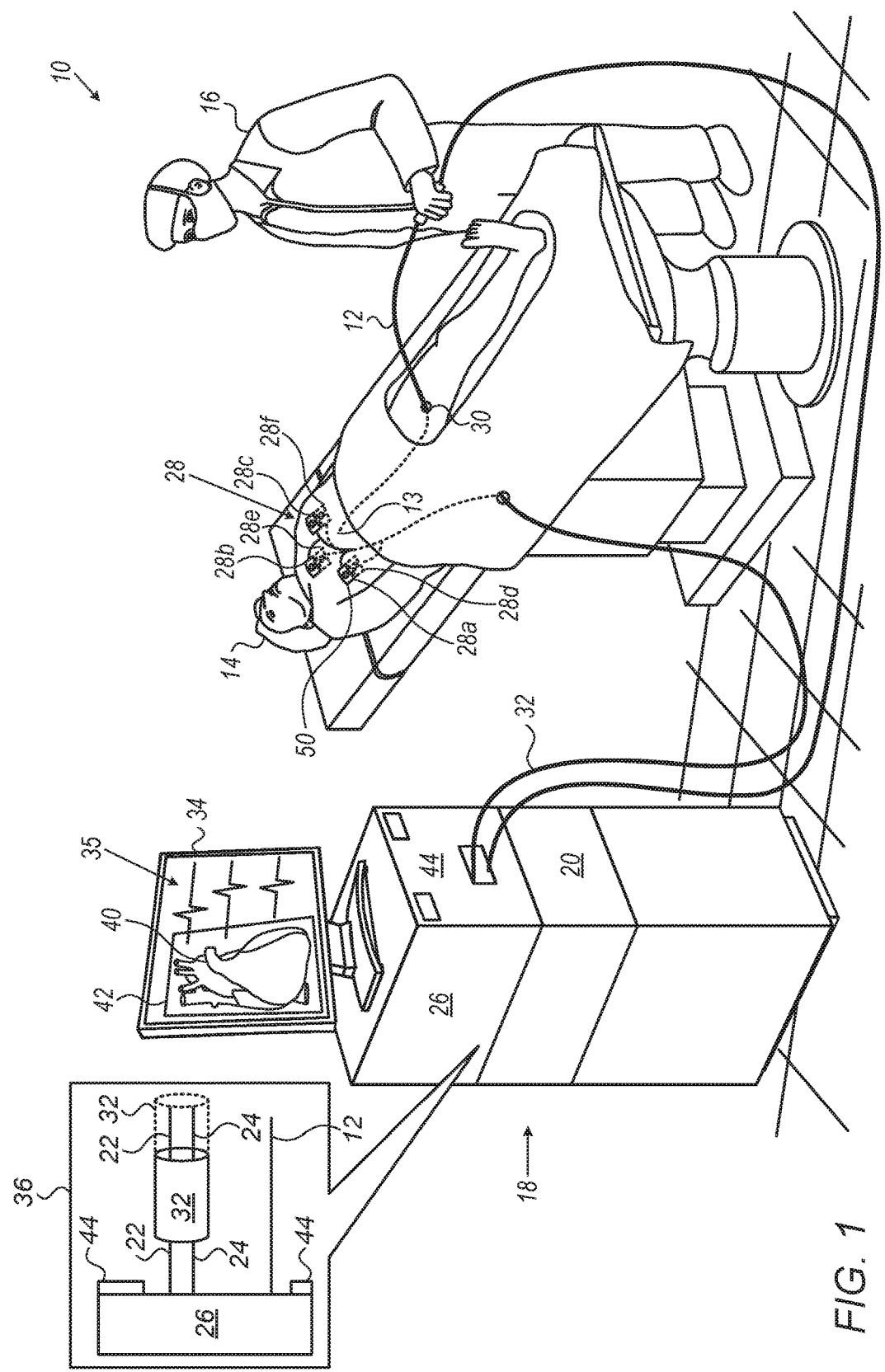
FIG. 1 is a schematic, pictorial illustration of a system for performing a medical procedure in a heart of a patient, in accordance with an embodiment of the present invention.

Embodiments of the present invention that are described hereinbelow provide techniques for simultaneously sensing, in a patch attached externally to a patient body, (i) electrocardiogram (ECG) signals received from the patient heart, and (ii) electrical signals indicative of an impedance between an electrode on the patch and a probe in the heart.

In some embodiments, the electrical signals are acquired, for example, for use in an active current location (ACL) system, configured to track a position of the probe in the heart. These signals are referred to herein as "ACL signals."

In principle, it is possible to use separate patches for sensing the ECG signals and the ACL signals. Using such patches, however, typically requires using separate sets, comprising at least three pairs of patches per set, for the ECG signals and for the ACL signals. In other words, at least twelve patches and twelve associated leads, or cables, may be attached to the patient in such procedures.

In some embodiments, the disclosed patch comprises an electrode, configured to sense both the ECG signals of the heart, and the ACL signals between the electrode and the probe in the heart. The output of the electrode comprises a superposition (i.e., sum) of the ACL signals and the ECG signals. In some embodiments, the patch further comprises circuitry, comprising an amplifier that is configured to amplify the output provided by the electrode, i.e., the ECG signals and the ACL signals, simultaneously.

ACL signals and ECG signals typically operate in different ranges of frequencies and amplitudes. ACL signals have a typical frequency on the order of 10 kilohertz (kHz) and a typical amplitude on the order of 1 millivolts (mv). The ECG signals have frequencies on the order of 1 hertz (Hz) and amplitudes on the order of 1 microvolt (μv). Designing a patch for sensing ACL signals and ECG signals simultaneously is challenging, e.g., because the large amplification required for the ECG signal may saturate the amplifier which will in turn distort the ACL signals.

In an embodiment, the amplifier has a very large dynamic range, and is configured to amplify the (typically strong) ACL signals and the (typically weak) ECG signals simultaneously. The amplifier saturation point is typically set so that the ACL signals are amplified to a required level without saturating the amplifier, thereby preventing distortion to the ACL signals. The noise figure of the amplifier is typically selected to be sufficiently small, so as to amplify the ECG signals with sufficient signal-to-noise ratio. The output of the amplifier, which comprises the superimposed amplified ECG and ACL signals, is referred to herein as an "amplified signal."

In some embodiments, the patch may further comprise an ACL filter, coupled to the amplifier output, and configured to filter the amplified ACL signals from the amplified signal to produce an ACL filtered signal. The patch additionally comprises an ECG filter coupled to the amplifier output, configured to filter the amplified ECG signals from the amplified signal, to produce an EGC filtered signal. In some embodiments, the filtered ACL signal and the filtered ECG signal are output from the patch to a processor via a single braid of leads/cables. Note that the ACL filter and the ECG filter cover respective first and second frequency ranges that differ from one another, and are typically non-overlapping.

The disclosed techniques enable reducing, e.g., by half, the number of patches and associated leads/cables required in medical procedures in which both ECG and ACL signals are sensed, thereby reducing the amount of patch-related skin irritation to the patient. Furthermore, the disclosed techniques reduce the amount of resources required in monitoring signals in the heart and in tracking the position of the probe in the heart.

System Description

FIG. 1 is a schematic, pictorial illustration of a system 10 for performing a medical procedure in a heart 40 of a patient 14, in accordance with an embodiment of the present invention. In some embodiments, system 10 comprises a probe, such as a catheter 12, comprising a distal tip 13 that comprises a plurality of devices (not shown), such as an impedance sensor and an ablation electrode.

During a cardiac procedure, a physician 16 may insert catheter 12, via an insertion point 30, into vasculature of patient 14, and may then navigate the catheter tip to heart 40. Subsequently, catheter 12 is used for monitoring electrical signals of heart 40.

In some embodiments, system 10 comprises an impedance-based active current location (ACL) system that may be used for tracking the position of distal tip 13 for the purpose of navigating catheter 12 to carry out a medical procedure, such as ablating selected locations within heart 40 of patient 14.

In some embodiments, the ACL system comprises a plurality of electrodes 28, which are coupled to the body of patient 14, e.g., via patches 50 that adhere to the skin of patient 14. In the example of FIG. 1, system 10 comprises six electrodes, of which electrodes 28a, 28b, and 28c are coupled to the front (e.g., chest) of patient 14, and electrodes 28d, 28e, and 28f are coupled to the back (e.g., torso) of patient 14.

As shown in FIG. 1, the electrodes are arranged in pairs as follows: electrodes 28a and 28d are facing one another on the right side of patient 14, electrodes 28c and 28f are facing one another on the left side of patient 14, and electrodes 28b and 28e are facing one another on the upper part of the chest and torso of patient 14.

As described above, electrodes 28 may be used for navigating catheter 12 within the body of patient 14, using impedance-based tracking techniques, such as those described, for example, in U.S. Pat. 8,456,182 and US Patent Application Publication 2015/0141798, whose disclosures are incorporated herein by reference. Such techniques involve estimating the location and orientation of distal tip 13 responsively to the different impedances measured between distal tip 13 and each of electrodes 28a-28f.

In some embodiments, the location and orientation of distal tip 13 at any given time, are typically estimated by applying an electrical signal of a known amplitude to distal tip 13, and the resulting voltages and/or currents are measured at each pair of electrodes 28. In alternative embodiments, the electrical signal may be applied by electrodes 28, and the resulting electrical values are measured by distal tip 13.

In some embodiments, these applied electrical signals cause the pairs of electrodes 28 (e.g., pair of electrodes 28a and 28d, electrodes 28c and 28f, and electrodes 28b and 28e), each of which is located at a different position relative to the catheter, to exhibit different respective electrical values, due to a different amount of electrically-impeding tissue (and therefore, a different degree of impedance) between distal tip 13 and each of the pairs of electrodes 28.

In the context of the present disclosure and in the claims, the terms "electrical value" "ACL signals" and "raw ACL signals" are used interchangeably, and refer to impedance, current, voltage, or to any other suitable electrical value indicative of the impedance between distal tip 13 and each of the pairs of electrodes 28.

In other embodiments, system 10 may comprise any suitable number of electrodes, coupled to the patient skin in any suitable arrangement.

In some embodiments, system 10 further comprises an electrocardiogram (ECG) system, configured to acquire electrical signals, indicative of the electrical activity of heart 40. In the context of the present disclosure and in the claims, the terms "ECG signals" and "raw ECG signals" are used interchangeably.

Note that electrodes 28 are configured to acquire, simultaneously, raw ACL signals and raw ECG signals (both signals shown in FIG. 2 below).

In some embodiments, system 10 comprises an operating console 18 comprising circuitry, such as an interface 26, configured to receive ECG signals and ACL signals acquired by electrodes 28 and distal tip 13. In some embodiments, the ECG signals and ACL signals acquired by electrodes 28 of patch 50 are routed to interface 26 via a braid 32 of leads, whereas distal tip 13 is connected to interface 26 via a cable running through catheter 12.

In the context of the present disclosure, the terms "leads" and "cables" are used interchangeably and refer to electrical conductors of the ECG signals and the ACL signals.

In some embodiments, console 18 comprises a processor 20, typically a general-purpose computer, with suitable front end and interface circuits for receiving ACL signals and ECG signals from interface 26, and for performing other operations of system 10 described herein. Processor 20 may be programmed in software to carry out the functions that are used by the system, and the processor stores data for the software in a memory (not shown). The software may be downloaded to console 18 in electronic form, over a network, for example, or it may be provided on non-transitory tangible media, such as optical, magnetic or electronic memory media. Alternatively, some or all of the functions of processor 20 may be carried out by dedicated or programmable digital hardware components.

Reference is now made to an inset 36. In some embodiments, braid 32 comprises at least two types of electrical leads, such as lead 22 and lead 24, which are configured to convey the ACL signals and ECG signals, respectively.

In some embodiments, the ACL signals are sent, via braid 32 and interface 26, to processor 20, which uses these values to estimate the relative location and orientation of distal tip 13 relative to electrodes 28 (whose positions are known). Alternatively, voltages between distal tip 13 of the catheter and the electrodes may be generated, and the resulting currents flowing through the electrodes, also referred to herein as "ACL signals," may be measured and used for tracking the position and orientation of distal tip 13.

Alternatively or additionally, the ACL signals acquired by distal tip 13 are conducted, via the cable of catheter 12 and interface 26, to processor 20.

In some embodiments, the ECG signals acquired by electrodes 28 are conducted, via one or more leads 24 of braid 32 and via interface 26, to processor 20.

Note that in this configuration, a single set of patches 50, and respective electrodes 28 are configured to conduct, simultaneously, the ECG signal and the ACL signals to interface 26, via a single braid of leads, such as braid 32.

In the example of FIG. 1, a single braid 32 of leads 22 and 24, and a single cable of catheter 12 are electrically connected to interface 26, through an opening in a front panel 44 of console 18. In other embodiments, any other configuration of braids or leads and/or cables may be applied. For example, braid 32 may comprise six leads 22 and six leads 24, extended from respective six electrodes 28a . . . f. These embodiments, reduce the amount of patches 50 adhered to the skin of patient 14, as well as the amount of electrodes 28. Furthermore, the twelve (12) leads, such as leads 22 and 24, extended from electrodes 28a . . . f, are incorporated into a single braid 32.

In an embodiment, the position of distal tip 13 is shown on an image 42 of heart 40, which is displayed on a user display 34. In some embodiments, image 42 is acquired using an anatomical imaging system, such as a computerized tomography (CT) system or any other suitable imaging technique.

Display 34, is typically configured to facilitate performance of the ablation procedure by displaying relevant information to physician 16. For example, processor 20 may register between the coordinate systems of the ACL systems and the coordinate system of the CT system (which acquired image 42), so as to display the position and orientation of distal tip 13 within image 42, e.g., by superimposing an icon representing distal tip 13 of catheter 12 over image 42 of heart 40.

In some embodiments, after processing the raw ECG signals acquired by electrodes 28, processor 20 is configured to display, on display 34, an ECG graphs 35, also known as "electrocardiograph," comprising the post-processed ECG signals, typically displayed as a graph of voltage versus time. Note that in this configuration, physician 16 can see on display 34, the position of distal tip 13 within heart 40 in conjunction with ECG graph 35 showing a continuous monitor of the ECG signals of heart 40.

In an alternative embodiment, instead of using separate leads 22 and 24, a single electrical lead may electrically connect between patch 50 and processor 20. In this embodiment, the single lead may conduct the ECG signals and the ACL signals, simultaneously, and any filtering of the ECG signals and the ACL signals is performed in console 18.

Simultaneously Monitoring ECG Signals and ACL Signals Using a Single Patch

Figure 2:
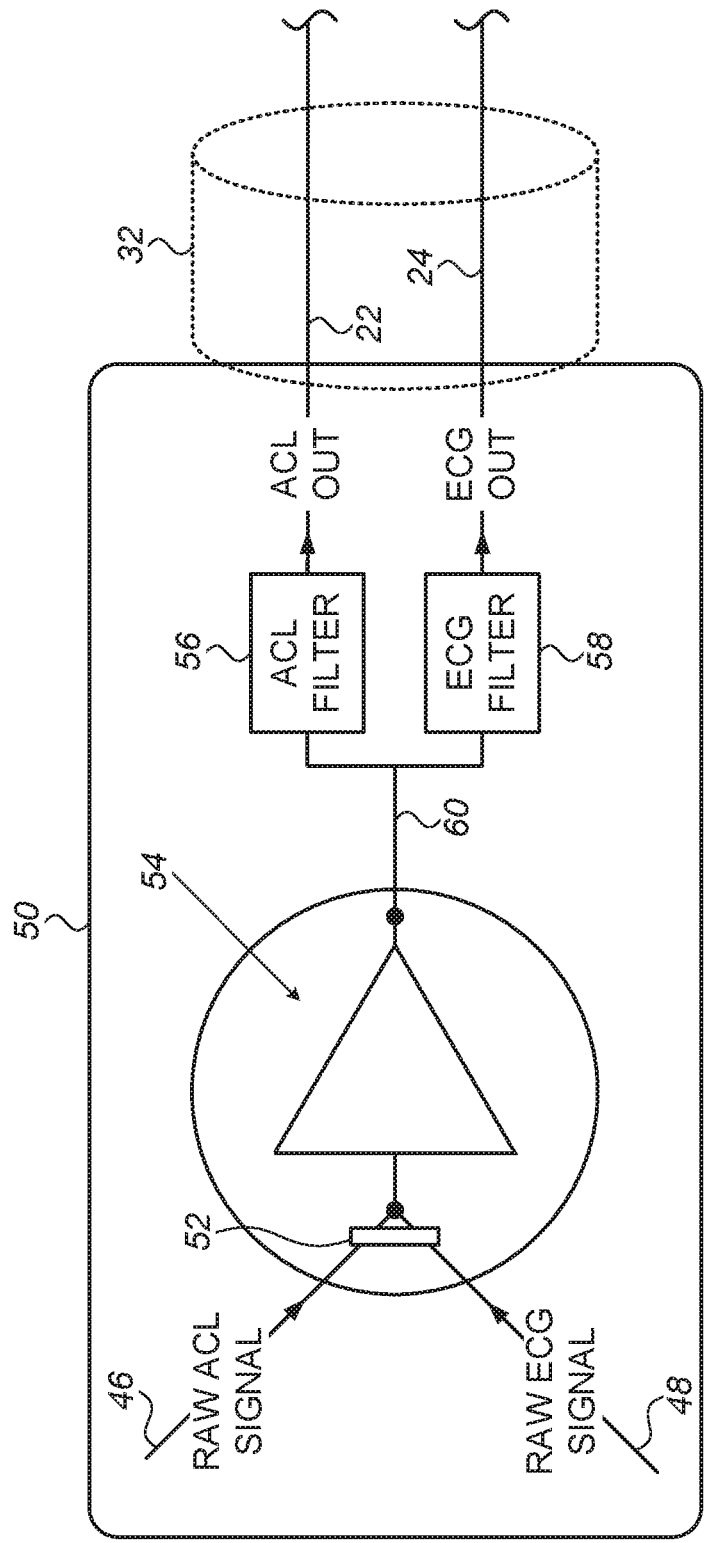
FIG. 2 is a schematic, pictorial illustration of a patch attached externally to a patient, for simultaneously sensing an electrocardiogram (ECG) signal and electrical signals indicative of an impedance between an electrode of the patch and a probe in the heart, in accordance with an embodiment of the present invention.

FIG. 2 is a schematic, pictorial illustration of a patch 50 for simultaneously acquiring raw ECG signals 46 and raw ACL signals 48, in accordance with an embodiment of the present invention.

In some embodiments, at least some of the elements of patch 50 shown in FIG. 2 and depicted herein, are coupled to a common substrate of patch 50 in any suitable configuration. For example, the elements may be mounted on the common substrate, attached below the common substrate, embedded inside the common substrate, fitted in a hole in the common substrate, or coupled to the common substrate of patch 50 in any other suitable configuration.

In an embodiment, the common substrate is configured to adhere to the skin of patient 14, and thereby, to attach at least some of the elements to the skin of patient 14.

In some embodiments, patch 50 comprises an electrode 52, configured to acquire both ECG signals 46 and ACL signals 48, simultaneously (in which case the ACL signals and ECG signals are sensed in parallel) or sequentially (in which case the ACL signals and the ECG signals are sensed at different time slots). Electrode 52 may replace for example, any electrode among electrodes 28a . . . f of FIG. 1 above.

Note that typical values of frequency and amplitude of the ACL signals are on the order of 10 kilohertz (kHz) and 1 millivolts (mv), respectively, whereas the respective values of frequency and amplitude of the ECG signals are on the order of 1 hertz (Hz) and 1 microvolt (µv).

In some embodiments, patch 50 comprises circuitry 54, which comprises an amplifier, such as INA103 produced by Texas Instruments (Dallas, Tex.). In an embodiment, circuitry 54 is configured to feed the amplifier with a combined signal comprising both ACL signals 46 and ECG signals 48, to be amplified simultaneously.

In some embodiments, amplifier 54 has a broad dynamic range that covers both amplitudes of ACL signals 46 and of ECG signals 48. The amplifier is configured to amplify the signal at its input so that both ACL signals 46 and ECG signals 48 are amplified linearly and with low noise. In other words, the broad dynamic range of the shared amplifier enables simultaneous amplification of ACL signals 46 and ECG signals 48 without saturating the amplifier by the ACL signals, and while providing acceptable signal-to-noise ratio for the ECG signals.

In some embodiments, patch 50 comprises an ACL filter 56 and an ECG filter 58, connected to circuitry 54 via one or more circuit traces 60. ACL filter 56 is configured to filter ACL signals 46 out of the amplified signal at the amplifier output. ECG filter 58 is configured to filter ECG signals 48 out of the amplified signal at the amplifier output. In some embodiments, ACL filter 56 comprises a band-pass filter (BPF) having a passband that matches the frequency range of the ACL signals. ECG filter 58 typically comprises a low-pass filter (LPF) having a cutoff frequency of several HZ or several tens of Hz.

In an embodiment, the filtered ACL signals and the filtered ECG signals are conducted from patch 50, via respective leads 22 and 24, to interface 26, as described in FIG. 1 above.

In another embodiment, ACL filter 56 and ECG filter 58 are contained in circuitry 54.

The configurations of system 10 and patch 50 presented in FIGS. 1 and 2, respectively, are simplified for the sake of clarity and are depicted purely by way of example. In alternative embodiments, any other suitable configurations can also be used. For example, in an alternative embodiment, filters 56 and 58 are located in console 18 and not on patch 50. In this embodiment, the amplified signal at the output of amplifier 54 (which comprises both the amplified ECG signals and the amplified ACL signals) is routed to console 18 over a single cable.

Although the embodiments described herein mainly address ECG signals and impedance-indicative electrical signals, the methods and systems described herein can also be used in other applications, such as in electroencephalogram (EEG) signals and brain mapping via electrodes.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical patch, comprising:
    a substrate, configured to attach externally to a patient;
    an electrode, which is coupled to the substrate and is configured to sense electrocardiogram (ECG) signals from a heart of the patient, and to further sense active current location signals (ACL) and
    circuitry, which is coupled to the substrate and comprises a shared amplifier that is configured to simultaneously amplify the ECG signals and the ACL signals,
    wherein the circuitry comprises an ECG filter and an ACL filter, which are configured to filter amplified ECG signals and amplified ACL signals, respectively,
    wherein the ACL filter comprises a band-pass filter (BPF) having a passband that matches a frequency range of the ACL signals, and the ECG filter comprises a low-pass filter (LPF) having a cutoff frequency of at least ten Hz.

2. The patch according to claim 1, wherein the ECG filter and an ACL filter cover respective first and second frequency ranges that differ from one another.

3. The patch according to claim 2, wherein the first and second frequency ranges are non-overlapping.

4. The patch according to claim 1, wherein the amplifier has a dynamic range that covers both amplitudes of the received ECG signals and of the received ACL signals.

5. A method for producing a medical patch, the method comprising:
    coupling, to a substrate configured to attach externally to a patient, an electrode for sensing electrocardiogram (ECG) signals from a heart of the patient, and for further sensing active current location (ACL) signals; and
    coupling to the substrate circuitry comprising a shared amplifier for simultaneously amplifying the ECG signals and the ACL signals
    wherein the circuitry comprises an ECG filter and an ACL filter, which are configured to filter amplified ECG signals and amplified ACL signals, respectively,
    wherein the ACL filter comprises a band-pass filter (BPF) having a passband that matches a frequency range of the ACL signals, and the ECG filter comprises a low-pass filter (LPF) having a cutoff frequency of at least ten Hz.

6. The method according to claim 5, wherein the ECG filter and an ACL filter cover respective first and second frequency ranges that differ from one another.

7. The method according to claim 6, wherein the first and second frequency ranges are non-overlapping.

8. The method according to claim 5, wherein the amplifier has a dynamic range that covers both amplitudes of the received ECG signals and of the received ACL signals.

* * * * *